United States Patent
Willcut et al.

(10) Patent No.: US 11,318,327 B2
(45) Date of Patent: *May 3, 2022

(54) ADAPTIVE RADIOTHERAPY SYSTEM

(71) Applicant: Elekta, Inc., Atlanta, GA (US)

(72) Inventors: Virgil Matthew Willcut, Kirkwood, MO (US); Michel Moreau, Verona, WI (US)

(73) Assignee: Elekta, Inc., Atlanta, GA (US)

( * ) Notice: Subject to any disclaimer, the term of this patent is extended or adjusted under 35 U.S.C. 154(b) by 152 days.

This patent is subject to a terminal disclaimer.

(21) Appl. No.: 16/665,360

(22) Filed: Oct. 28, 2019

(65) Prior Publication Data

US 2020/0061389 A1  Feb. 27, 2020

Related U.S. Application Data

(63) Continuation of application No. 15/697,667, filed on Sep. 7, 2017, now Pat. No. 10,485,990.

(51) Int. Cl.
*A61N 5/10* (2006.01)
*G06T 3/00* (2006.01)
(Continued)

(52) U.S. Cl.
CPC ......... *A61N 5/1039* (2013.01); *A61N 5/1031* (2013.01); *A61N 5/1077* (2013.01);
(Continued)

(58) Field of Classification Search
CPC .... A61N 5/103; A61N 5/1031; A61N 5/1039; A61N 5/1077
See application file for complete search history.

(56) References Cited

U.S. PATENT DOCUMENTS 10,485,990 B2 * 11/2019 Willcut ............... A61N 5/1039
2014/0201670 A1  7/2014 Mallya et al.
(Continued)

FOREIGN PATENT DOCUMENTS

CN   101341516   1/2009
CN   103782320   5/2014
(Continued)

OTHER PUBLICATIONS

"International Application Serial No. PCT US2018 049541, International Preliminary Report on Patentability dated Mar. 19, 2020", 9 pgs.
(Continued)

*Primary Examiner* — John P Lacyk
(74) *Attorney, Agent, or Firm* — Schwegman Lundberg & Woessner, P.A.

(57) ABSTRACT

The present disclosure relates to a method for use in adaptive radiotherapy and a treatment planning device. The method may comprise accessing a first medical image and a second medical image that represent a region of interest of a patient at different times. Each medical image is segmented into a target region and at least one non-target region. The method may further comprise accessing a deformation vector field including a plurality of vectors, wherein each vector defines a geometric transformation to map a respective voxel in the first medical image to a corresponding voxel in the second medical image. The method may further comprise generating a modified deformation vector field by: identifying a first vector in the deformation vector field that maps a voxel in the first medical image to a voxel that is in a non-target region in the second medical image; and determining whether the first vector causes a distance between the mapped voxel and the target region to increase and, if so, reducing the magnitude of the first vector. The method may
(Continued)

further comprise post-processing the modified deformation vector field to compensate for changes in the shape or size of the target region.

24 Claims, 12 Drawing Sheets

(51) Int. Cl.
  *G06T 7/00* (2017.01)
  *G06T 7/11* (2017.01)
  *G06T 7/30* (2017.01)

(52) U.S. Cl.
  CPC .......... *G06T 3/0081* (2013.01); *G06T 7/0014* (2013.01); *G06T 7/0016* (2013.01); *G06T 7/11* (2017.01); *G06T 7/30* (2017.01); *G06T 2207/30036* (2013.01); *G06T 2207/30088* (2013.01); *G06T 2207/30096* (2013.01)

(56) References Cited

U.S. PATENT DOCUMENTS

| | | |
|---|---|---|
| 2015/0317788 A1 | 11/2015 | Van Baar et al. |
| 2016/0279444 A1 | 9/2016 | Schlosser |
| 2017/0072220 A1 | 3/2017 | Zankowski et al. |
| 2019/0070436 A1 | 3/2019 | Willcut et al. |

FOREIGN PATENT DOCUMENTS

| | | |
|---|---|---|
| CN | 104408734 | 3/2015 |
| CN | 111344737 | 6/2020 |
| CN | 113577577 | 11/2021 |
| JP | 2014531634 | 11/2014 |
| WO | 2014201670 | 12/2014 |
| WO | 2015085252 | 6/2015 |
| WO | 2016069633 | 5/2016 |
| WO | 2016094284 | 6/2016 |
| WO | WO-2019050945 A1 | 3/2019 |

OTHER PUBLICATIONS

"Australian Application Serial No. 2018330066, Office Action dated Sep. 15, 2020", 3 pgs.
"Japanese Application Serial No. 2020-513805, Notification of Reasons for Rejection dated Sep. 29, 2020", W English Translation, 5 pgs.
"European Application Serial No. 18782568.2 Response to Communication pursuant to Rules 161(1) and 162 EPC filed Oct. 26, 2020", 18 pgs.
"Japanese Application Serial No. 2020-513805, Response filed Nov. 19, 2020 to Notification of Reasons for Rejection dated Sep. 29, 2020", w English claims, 15 pgs.
"Chinese Application Serial No. 201880058231.4, Office Action dated Nov. 3, 2020", w English Translation, 17 pgs.
"Australian Application Serial No. 2018330066, Office Action dated Sep. 15, 2020", 38 pgs.
"Chinese Application Serial No. 201880058231.4, Response filed Mar. 18, 2021 to Office Action dated Nov. 3, 2020", w English claims, 19 pgs.
"European Applicatoion Serial No. 18782568.2, Communication Pursuant to Article 94(3) EPC dated Feb. 25, 2021", 6 ogs.
"European Applicatoion Serial No. 18782568.2, Response filed May 13, 2021 to Communication Pursuant to Article 94(3) EPC dated Feb. 25, 2021", 17 pgs.
"U.S. Appl. No. 15/697,667, Notice of Allowance dated Jun. 25, 2019", 8 pgs.
"U.S. Appl. No. 15/697,667, Notice of Allowance dated Jul. 25, 2019", 7 pgs.
"International Application Serial No. PCT/US2018/049541, International Search Report dated Jan. 16, 2019", 4 pgs.
"International Application Serial No. PCT/US2018/049541, Written Opinion dated Jan. 16, 2019", 7 pgs.
Carri, Glide-Hurst K, et al., "Improving radiotherapy planning, delivery accuracy, and normal tissue sparing using cutting edge technologies", Journal of thoracic disease, (Apr. 1, 2014), 303-318.
John, Gordon Eley, et al., "4D optimization of scanned ion beam tracking therapy for moving tumors", Physics in Medicine and Biology Institute of Physics Publishing Bristol GB vol. 59 No. 13, (Jun. 3, 2014), 3431-3452.
Murphy, Martin J, et al., "A method to estimate the effect of deformable image registration uncertainties on daily dose mapping", Medical Physics Alp Melville NY US vol. 39 No 2, (Feb. 1, 2012), 573-580.
Veiga, Catarina, et al., "Toward adaptive radiotherapy for head and neck patients: Uncertainties in dose warping due to the choice of deformable registration algorithm", Medical Physics AIP Melville NY US vol. 42 No. 2, (Feb. 28, 2015), 760-769.
"Australian Application Serial No. 2020264304, First Examination Report dated Oct. 11, 2021", 2 pgs.
"Japanese Application Serial No. 2021-000756, Notification of Reasons for Rejection dated Nov. 2, 2021", W English Translation, 6 pgs.
"Australian Application Serial No. 2020264304, Response filed Nov. 17, 2021 to First Examination Report dated Oct. 11, 2021", 23 pgs.
"Japanese Application Serial No. 2021-000756, Response filed Jan. 21, 2022 to Notification of Reasons for Rejection dated Nov. 2, 2021", w English Claims, 15 pgs.

\* cited by examiner

ADAPTIVE RADIOTHERAPY SYSTEM

CLAIM FOR PRIORITY

This application claims the benefit of priority to U.S. patent application Ser. No. 15/697,667, filed on Sep. 7, 2017, which hereby is incorporated by reference in its entirety.

TECHNICAL FIELD

This disclosure generally relates to radiation therapy. More specifically, but without limitation, the disclosure relates to a system and method for use in adaptive radiotherapy.

BACKGROUND

Radiation therapy, also known as radiotherapy, is used to treat tumors and other ailments in mammalian (e.g., human and animal) tissue. An example of a radiotherapy treatment would be the application of a high-energy beam from an external source towards a patient to produce a collimated beam of radiation directed to a target site of a patient. The target may be a region of the patient's body that contains a diseased organ or tumor that is to be exposed to, and treated by, the radiation beam. The placement and dose of the radiation beam must be accurately controlled to ensure that the target receives the dose of radiation that has been prescribed for the patient by a physician yet damage to the surrounding healthy tissue, often called the organ(s) at risk (OARs), is minimized.

To plan a patient's radiotherapy treatment one or more medical images of the patient in the intended treatment position are acquired prior to a radiation therapy treatment session and are often acquired many days before the initiation of treatment. These are referred to as planning images.

Physicians can use the planning images to identify and contour a target or targets as well as OARs. Contouring can be performed manually, semi-automatically, or automatically. A treatment contour, often referred to as a planned target volume (PTV), is created which includes the target contour plus sufficient margins to account for microscopic disease as well as treatment uncertainties. A radiation dose is prescribed by the physician, and a radiation therapy treatment plan is created that optimally delivers the prescribed dose to the PTV while minimizing dose to the OARs and other normal tissues. The treatment plan can be generated manually by the physician, or can be generated automatically using an optimization technique. The optimization technique may be based on clinical and dosimetric objectives and constraints (e.g., the maximum, minimum, and mean doses of radiation to the tumor and OARs).

A treatment course is developed to deliver the prescribed dose over a number of fractions, wherein each fraction is delivered in a different treatment session. For example, 30-40 fractions are typical, but five or even one fraction can be used. Fractions are typically delivered once, or in some cases twice, per weekday. In some cases, the radiation treatment plan can change throughout the course to focus more dose in some areas.

At each fraction, the patient is set up on a patient support accessory (often referred to as the "couch") of a radiation therapy device, and repositioned as closely as possible to their position in the planning images. Unfortunately, this is a difficult task to carry out accurately in practice, because the patient is not a rigid object and the patient's anatomy can move or change. Fraction-to-fraction variations or changes are often referred to as interfractional variations, while variation or changes occurring during a fraction itself are often referred to as intrafractional variations.

Image-guided radiotherapy (IGRT) attempts to minimize the problem of interfractional variation. IGRT involves acquiring one or more medical images of the patient shortly before radiation therapy, and using those images to identify and compensate for interfractional variation. As opposed to planning images, which can be acquired on any diagnostic scanner, IGRT images are acquired directly in the treatment room, while the patient is in the treatment position. To compensate for interfractional variation, IGRT images are compared with the planning images to quantify changes in the patient's anatomy that have occurred since the planning images were generated. For example, the planning images and IGRT images may be analyzed to calculate a global shift and/or rotation that best aligns the planning images to the IGRT images. Once the shift and/or rotation have been calculated, a corresponding adjustment to the position of the patient support accessory can be made, such that the position of the patient during the treatment session more closely matches the position of the patient when the planning images were acquired. Note that in this scenario, the original plan is still delivered, and only the patient's position has been changed to minimize the deviation from what was planned.

Adaptive radiotherapy is another technique that aims to solve the problem of interfractional variation. As with IGRT, adaptive radiotherapy involves acquiring one or more medical images of the patient shortly before a radiation therapy treatment session, and using those images to identify and compensate for interfractional variation. However, in adaptive radiotherapy, not only may the patient's position be changed, but the plan itself may be adapted to account for interfractional variations. In adaptive radiotherapy, the planning images and the images taken shortly before the treatment session may be analyzed to generate a deformation vector field (DVF). The DVF is a 3D array whose elements are vectors, and in which each vector defines a geometric transformation to map a voxel in a planning image to the corresponding voxel in an image taken shortly before the treatment session. This DVF can be used to transform the spatial distribution of the radiation dose prescribed in the original treatment plan, in order to account for changes in the patient's anatomy that have occurred since the planning images were acquired. This transformed dose distribution results in a dose distribution that is equivalent to the approved dose distribution from the original, approved treatment plan and may be used as a "goal" dose for a replanning activity, with the idea being if one can find a plan that achieves this transformed dose distribution, then the physician's original goals will be met. However, using this transformed dose as the goal does not allow for the plan to be better than what the physician originally requested, if the anatomical variations are favorable, it simply reproduces a plan as good as what was originally planned, assuming that is physically achievable. To illustrate "favorable anatomical variations", consider the case where all the OARs move further away from the target. Clearly in this case, it is geometrically much easier to treat the target just as intended (to the same dose level), but deliver less dose to the OARs. A solution would be to apply some logic so that when an OAR or portion of an OAR moves further from the target, the DVF is processed (modified) to constrain the distance to remain constant. Using this processed DVF to transform the dose would result in a goal dose distribution that maintained the same target dose and target conformality, but demonstrated lower doses to those OARs or portions of OARs that in reality were further from the target(s).

SUMMARY

A first aspect of the present disclosure provides a processor-implemented method for use in adaptive radiotherapy. The method may comprise accessing a first medical image and a second medical image, the first and second medical images representing a region of interest of a patient at different times, wherein each medical image includes a plurality of voxels and is segmented into one or more target regions and one or more non-target regions. The method may further comprise accessing a DVF, the DVF including a plurality of vectors, wherein each vector defines a geometric transformation to map a respective voxel in the first medical image to a corresponding voxel in the second medical image. The method may further comprise generating a modified DVF. Generating the modified DVF may include identifying a first vector in the DVF that maps a non-target voxel in the first medical image to the corresponding non-target voxel in the second medical image. Generating the modified DVF may further include determining whether the first vector causes a distance between the mapped voxel and the mapped target region to increase when compared to the original voxel's distance from the original target region. Generating the modified DVF may further include, when it is determined that the first vector causes the distance between the mapped voxel and the mapped target region to increase, generating a modified first vector by reducing the magnitude of the first vector such that the distance between the mapped voxel and the mapped target region is not increased relative to the voxel's original distance from the original target region. Generating the modified DVF may further include storing the modified first vector in the modified DVF.

A further aspect of the present disclosure provides a radiation therapy device. The radiation therapy device may comprise a hardware processor and a memory device coupled to the hardware processor. The memory device may store instructions that, when executed by the hardware processor, cause the hardware processor to perform a method that comprises accessing a first medical image and a second medical image, the first and second medical images representing a region of interest of a patient at different times, wherein each medical image includes a plurality of voxels and is segmented into a at least one target region and at least one non-target region. The method may further comprise accessing a DVF, the DVF including a plurality of vectors, wherein each vector defines a geometric transformation to map a respective voxel in the first medical image to a corresponding voxel in the second medical image. The method may further comprise generating a modified DVF. Generating the modified DVF may include identifying a first vector in the DVF that maps a non-target voxel in the first medical image to the corresponding non-target voxel in the second medical image. Generating the modified DVF may further include determining whether the first vector causes a distance between the mapped voxel and the mapped target region to increase relative to the original voxel's distance from the original target region. Generating the modified DVF may further include, when it is determined that the first vector causes the distance between the mapped voxel and the mapped target region to increase, generating a modified first vector by reducing the magnitude of the first vector such that the distance between the mapped voxel and the mapped target region is not increased. Generating the modified DVF may further include storing the modified first vector in the modified DVF.

A further aspect of the present disclosure provides a non-transitory computer-readable medium comprising instructions that, when executed by a processor, cause the processor to perform a method comprising accessing a first medical image and a second medical image, the first and second medical images representing a region of interest of a patient at different times, wherein each medical image includes a plurality of voxels and is segmented into a target region and at least one non-target region. The method may further comprise accessing a DVF, the DVF including a plurality of vectors, wherein each vector defines a geometric transformation to map a respective voxel in the first medical image to a corresponding voxel in the second medical image. The method may further comprise generating a modified DVF. Generating the modified DVF may include identifying a first vector in the DVF that maps a non-target voxel in the first medical image to the corresponding non-target voxel in the second medical image. Generating the modified DVF may further include determining whether the first vector causes a distance between the mapped voxel and the mapped target region to increase. Generating the modified DVF may further include, when it is determined that the first vector causes the distance between the mapped voxel and the mapped target region to increase relative the voxel's original distance from the original target region, generating a modified first vector by reducing the magnitude of the first vector such that the distance between the mapped voxel and the mapped target region is not increased. Generating the modified DVF may further include storing the modified first vector in the modified DVF.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the invention, as claimed.

BRIEF DESCRIPTION OF THE DRAWINGS

The accompanying drawings, which constitute a part of this specification, illustrate several embodiments and, together with the description, serve to explain the disclosed principles.

Figure 9:
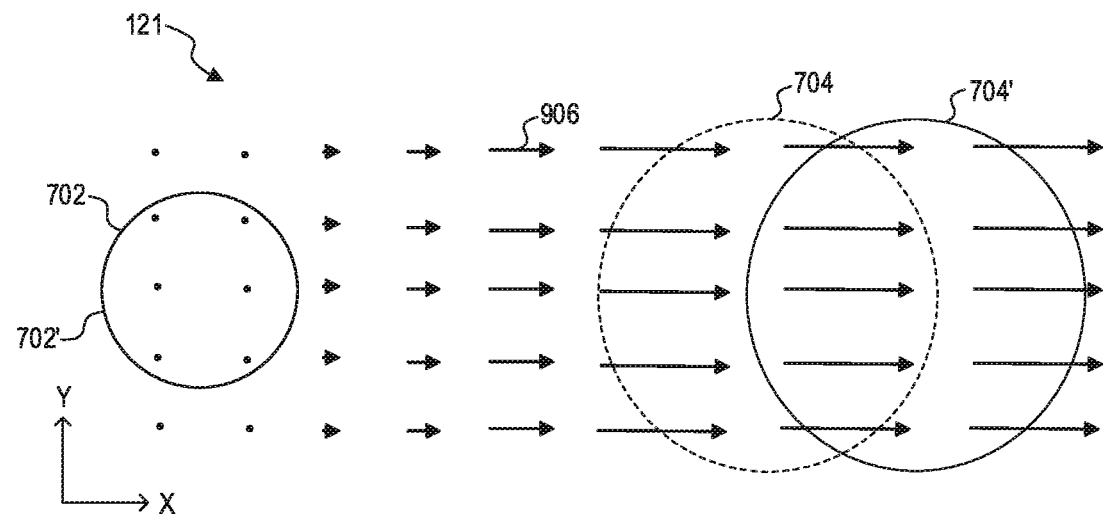
FIG. 9 illustrates a deformation vector field to map the medical image of FIG. 7 to the medical image of FIG. 8.
Figure 10:
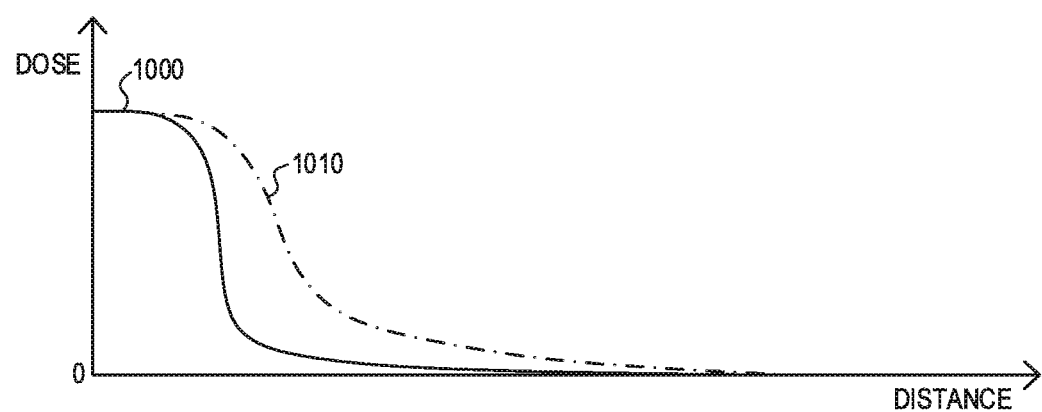
FIG. 10 illustrates exemplary dose distributions before and after transformation by the deformation vector field of FIG. 9.

9 illustrates a modified DVF generated by the method of FIG. 10 illustrates dose distributions before and after transformation by the DVF of FIG. 9.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Exemplary embodiments generally relate to adapting a treatment plan to compensate for variation of a patient's anatomy that can occur during the period of time between acquisition of a planning image and a radiation therapy treatment session. This is achieved by modifying a DVF to reduce the magnitude of vectors that cause voxels to move away from one or more target regions that are to be treated by exposure to radiation. The modified DVF may be used to transform a dose distribution, which may be used as a goal dose to generate a new treatment plan. The new treatment plan may ensure that the target receives the prescribed dose of radiation despite variation of the patient's anatomy, and may reduce the exposure to radiation of healthy tissue surrounding the target.

Figure 1:
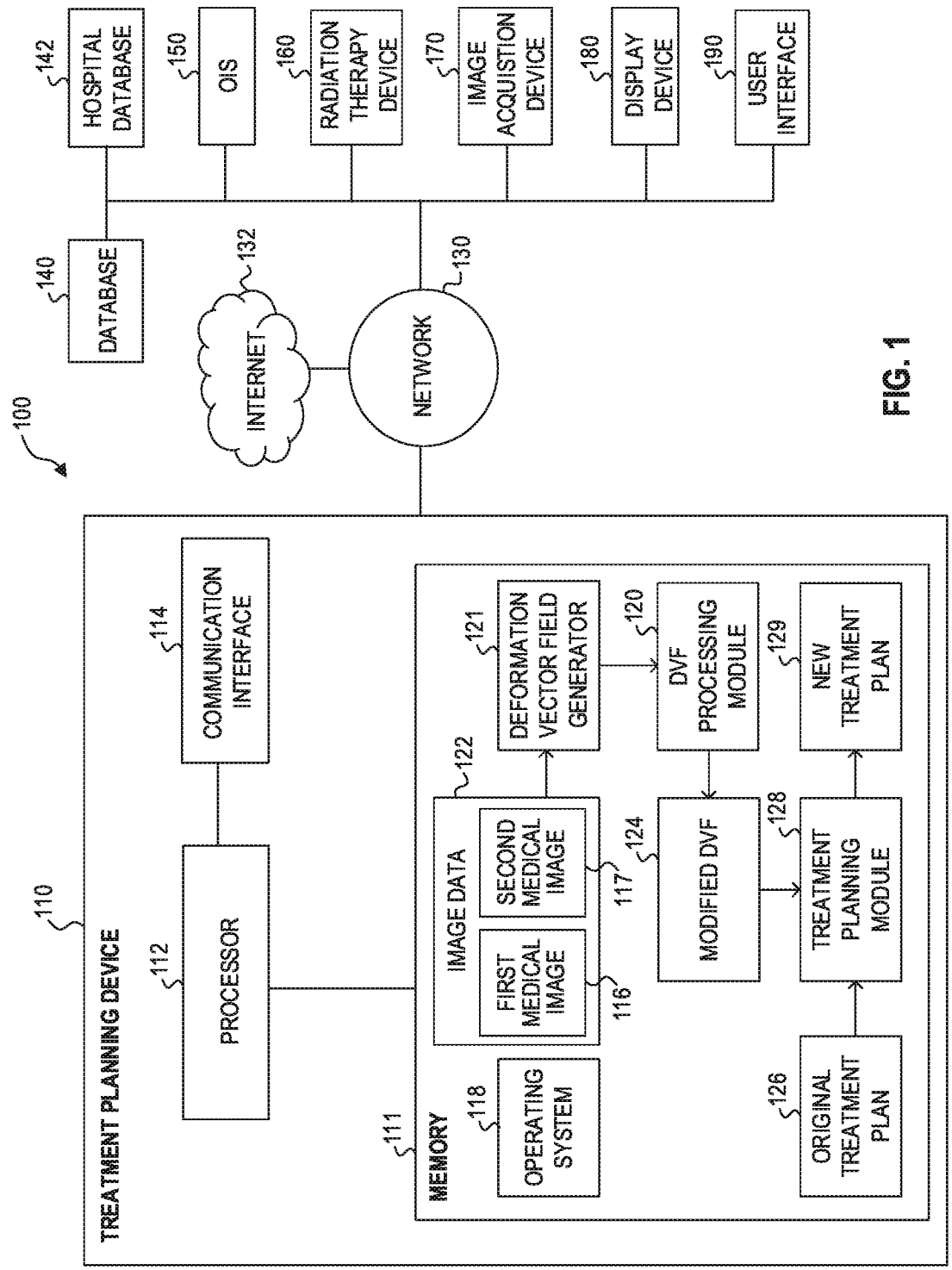
FIG. 1 illustrates an exemplary system for adaptive radiotherapy.

FIG. 1 illustrates an exemplary radiotherapy system 100 for performing adaptive radiotherapy. The radiotherapy system 100 includes a treatment planning device 110. The treatment planning device 110 may be connected to a network 130. The network 130 may be connected to the Internet 132. The network 130 can connect the treatment planning device 110 with one or more of a database 140, a hospital database 142, an oncology information system (OIS) 150, a radiation therapy device 160, an image acquisition device 170, a display device 180 and/or a user interface 190. The treatment planning device 110 is configured to generate radiation therapy treatment plans to be used by the radiation therapy device 160.

The treatment planning device 110 may include a memory device 111, a processor 112 and a communication interface 114. The memory device 111 may store computer-executable instructions, such as an operating system 118, a DVF processing module 120, a treatment planning module 128 and any other computer executable instructions to be executed by the processor 112. The memory device 111 may store data, including image data 122, a DVF 121, a modified DVF 124, an original treatment plan 126 and a new treatment plan 129.

The processor 112 may be communicatively coupled to the memory device 111, and the processor 112 may be configured to execute computer executable instructions stored thereon. For example, the processor 112 may execute the DVF processing module 120. The operation of the DVF processing module 120 is described below, with reference to FIG. 8. In addition, the processor 112 may execute the treatment planning module 128, which may interface with the DVF processing module 120.

The processor 112 may be a processing device, include one or more general-purpose processing devices such as a microprocessor, a central processing unit (CPU), a graphics processing unit (GPU), an accelerated processing unit (APU), or the like. More particularly, the processor 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 112 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 112 may be a special-purpose processor, rather than a general-purpose processor. The processor 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 112 may also include accelerated processing units such as the Desktop A-4(6,8) Series manufactured by AMD™, the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processor 112 can execute sequences of computer program instructions, stored in memory 111, to perform various operations, processes, methods that will be explained in greater detail below.

The memory device 111 can store image data 122 (e.g., 3D MRI, 4D MRI, 3D CT, 4D CT, 3D ultrasound, 4D ultrasound, 2D slices, etc.) received from the image acquisition device 170, or any other type of data/information in any format that the treatment planning device 110 may use to perform operations consistent with the disclosed embodiments. The memory device 111 may include a read-only memory (ROM), a flash memory, a random access memory (RAM), a dynamic random access memory (DRAM) such as synchronous DRAM (SDRAM), a static memory (e.g., flash memory, static random access memory) etc., on which computer executable instructions are stored in any format. The computer program instructions can be accessed by the processor 112, read from the ROM, or any other suitable memory location, and loaded into the RAM for execution by the processor 112. For example, the memory 111 may store one or more software applications. Software applications stored in the memory 111 may include, for example, an operating system 118 for common computer systems as well as for software-controlled devices. Further, the memory 111 may store an entire software application or only a part of a software application that is executable by the processor 112. For example, the memory device 111 may store a treatment planning module 128. The memory device 111 may also store one or more radiation therapy treatment plans 126, 129 generated by the treatment planning module 128.

In some embodiments, memory device 111 may include a processor-readable storage medium (not shown in FIG. 1). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

The treatment planning device 110 can communicate with the network 130 via the communication interface 114, which is communicatively coupled to the processor 112 and memory 111. Communication interface 114 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 114 may include one or more digital and/or analog communication devices that permit treatment planning device 110 to communicate with other machines and devices, such as remotely located components, via a network 130.

The network 130 may provide the functionality of a local area network (LAN), a wireless network, a cloud computing environment (e.g., software as a service, platform as a service, infrastructure as a service, etc.), a client-server, a wide area network (WAN), and the like. Therefore, network 130 can allow data transmission between the treatment planning device 110 and a number of various other systems and devices, such as the OIS 150, the radiation therapy device 160 and the image acquisition device 170. Further, data generated by the OIS 150 and/or the image acquisition device 170 may be stored in the memory 111, the database 140 and/or the hospital database 142. The data may be transmitted/received via network 130, through communication interface 114 in order to be accessed by the processor 112, as required.

The treatment planning device 110 may communicate with database 140 through network 130 to send/receive a plurality of various types of data stored on database 140. For example, the database 140 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, etc.) from image acquisition device 170. Database 140 may store data to be used by the DVF processing module 120 and the treatment planning module 128. The treatment planning device 110 may receive the imaging data (e.g., 3DMRI images, 4D MRI images) from the database 140 to order to generate a DVF 121, 124 and a treatment plan 126, 129.

Further, the radiotherapy system 100 can include an image acquisition device 170 that can acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 170 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the imaging acquisition device 170 can be stored within database 140 as either imaging data and/or test data. By way of example, the images acquired by the imaging acquisition device 170 can be also stored by the treatment planning device 110, as image data 122 in memory 111.

In an embodiment, for example, the image acquisition device 170 may be integrated with the radiation therapy device 160 as a single apparatus (e.g., a MRI device combined with a linear accelerator, also referred to as an "MRI-Linac", or as an MRI device combined with a Gamma Knife). Such an MRI-Linac can be used, for example, to determine a location of a target organ or a target tumor in the patient, so as to direct radiation therapy accurately according to the radiation therapy treatment plan to a predetermined target.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processor 112 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 170 in "real-time" while a patient is undergoing radiation therapy treatment, for example, when using the radiation therapy device 160.

The treatment planning device 110 may generate and store radiation therapy treatment plans 126, 129 for one or more patients. The treatment planning device 110 may provide information about a particular radiation dose to be applied to each patient. The treatment planning device 110 may also generate and/or store other radiotherapy information, such as beam angles, dose-histogram-volume information, the number of radiation beams to be used during therapy, the dose per beam, and the like.

Generating the treatment plan 126, 129 may include communicating with the image acquisition device 170 (e.g., a CT device, a MRI device, a PET device, an X-ray device, an ultrasound device, etc.) in order to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the treatment planning device 110 may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 170 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker) or automatically (e.g., using a program such as the Atlas-based auto-segmentation software, ABAS®, manufactured by Elekta AB of Stockholm, Sweden). In certain embodiments, the 3D structure of a target tumor or an OAR may be generated automatically by the treatment planning device 110.

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45Gy, ≤55Gy and <54Gy, respectively). The result of inverse planning may constitute a radiation therapy treatment plan 126 that may be stored in the treatment planning device 110 or database 140. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the treatment planning device 110 can generate a tailored radiation therapy treatment plan 126 having these parameters in order for the radiation therapy device 160 to provide radiotherapy treatment to the patient.

In addition, the radiotherapy system 100 may include a display device 180 and a user interface 190. The display device 180 may include one or more display screens that display medical images, interface information, treatment planning parameters (e.g., contours, dosages, beam angles, etc.) treatment plans, a target, localizing a target and/or tracking a target, or any related information to the user. The user interface 190 may be a keyboard, a keypad, a touch screen or any type of device that a user may input information to radiotherapy system 100.

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the treatment planning device 110, the OIS 150, the image acquisition device 170 could be implemented as a virtual machine. Given the processing power, memory, and computational capability available, the entire radiotherapy system could be implemented as a virtual machine.

Figure 2:
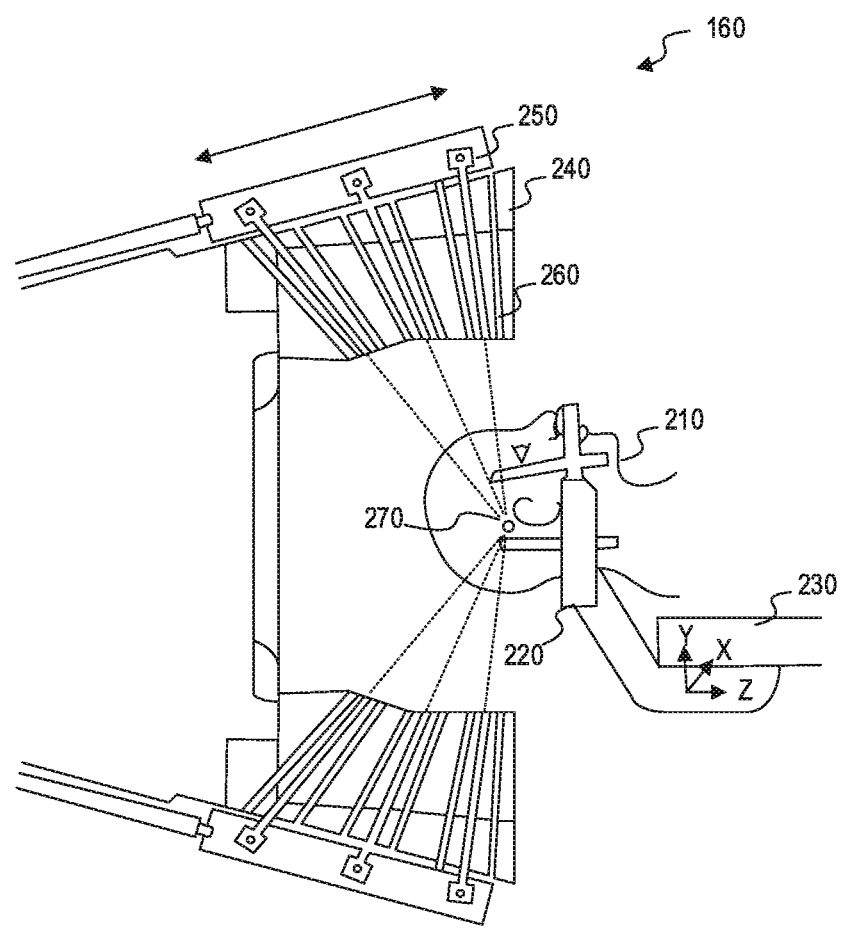
FIG. 2 illustrates an example of a radiation therapy device, known as a Gamma Knife, which may be used in the adaptive radiotherapy system of FIG. 1.

FIG. 2 illustrates an example of one type of radiation therapy device 160. The example in FIG. 2 is a Leksell Gamma Knife, manufactured by Elekta AB of Stockholm, Sweden. The Gamma Knife can be configured to use a treatment plan 126, 129 (shown in FIG. 1) to treat a target tumor in the brain. In an embodiment, an MRI apparatus, as an image acquisition device 170, can be integrated with the Gamma Knife. As shown in FIG. 2, during a radiation therapy treatment session, a patient 210 may wear a coordinate frame 220 to keep stable the patient's body part (e.g., the head) undergoing surgery or radiotherapy. Coordinate frame 220 and a patient positioning system 230 may establish a spatial coordinate system, which may be used while imaging a patient or during radiation surgery. The Gamma Knife may include a protective housing 240 to enclose a plurality of radiation sources 250. Radiation sources 250 may generate a plurality of radiation beams (e.g., beamlets) through beam channels 260. The plurality of radiation beams may be configured to focus on an isocenter 270 (ideally corresponding to the tumor location) from different directions. While each individual radiation beam may have a relatively low intensity, isocenter 270 may receive a relatively high level of radiation when multiple doses from different radiation beams accumulate at isocenter 270. In certain embodiments, as noted above, isocenter 270 may correspond to a target under surgery or treatment, such as a tumor.

Figure 3:
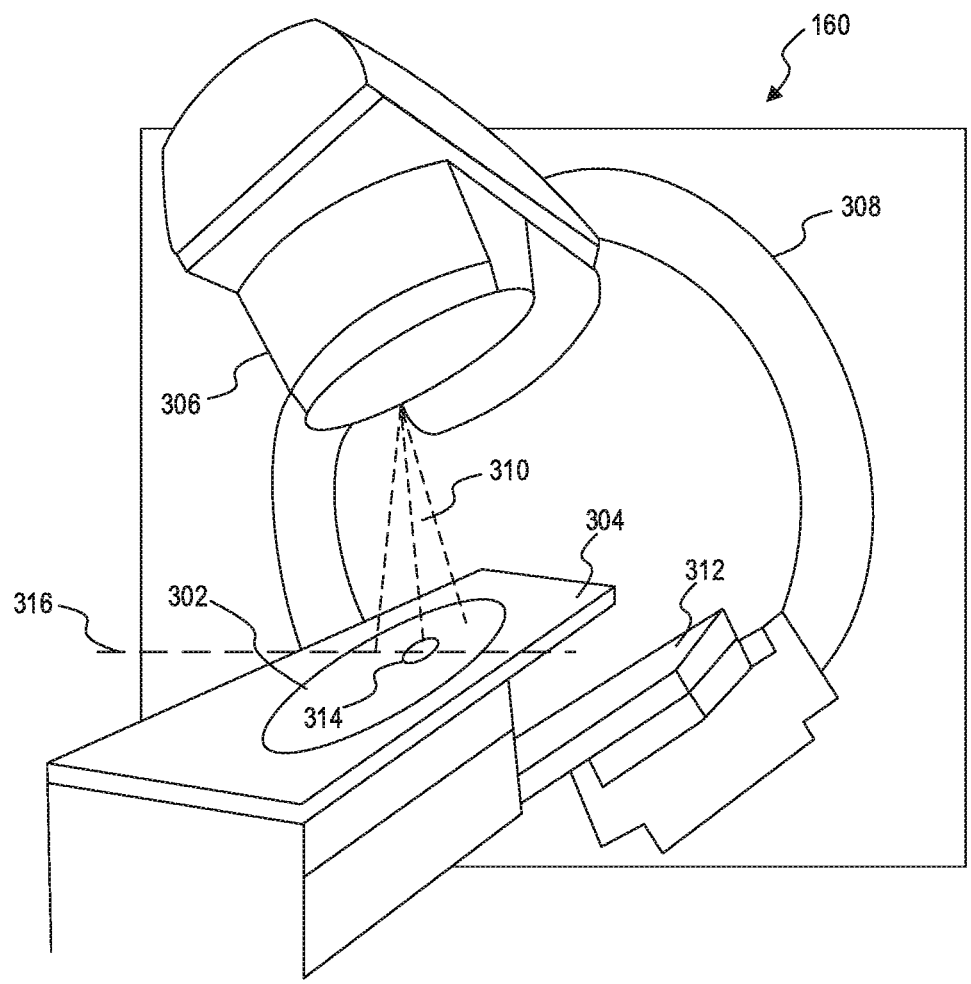
FIG. 3 illustrates another example of a radiation therapy device, a linear accelerator, which may be used in the adaptive radiotherapy system of FIG. 1.

FIG. 3 illustrates another example of a type of radiation therapy device 160. The example illustrated in FIG. 3 is a linear accelerator, or "Linac", manufactured by Elekta AB of Stockholm, Sweden. Using the linear accelerator, a patient 302 may be positioned on a patient table 304 to receive the radiation dose determined by a radiation therapy treatment plan 126, 129 generated by the treatment planning device 110 (shown in FIG. 1) to treat a target organ or a target tumor located within the anatomy of the patient 302.

The linear accelerator may include a radiation head 306 connected to a gantry 308 that rotates around the patient 302. The radiation head 306 generates a radiation beam 310 that is directed toward the target organ or target tumor. As the gantry 308 rotates, the radiation head 306 can rotate around the patient 302. While rotating, the radiation head 306 may provide patient 302 with a plurality of varying dosages of radiation depending upon the angle and the shape and size of the tumor according to a treatment plan 126, 129 generated by the treatment planning device 110 (shown in FIG. 1).

In addition, below the patient table 304, a flat panel scintillator detector 312 may be provided, which may rotate synchronously with the radiation head 306 around an isocenter 314 located on a target organ or a target tumor on the body of the patient 302. The flat panel scintillator 312 can acquire images and be used for verification of the amount of radiation received by the patient 302 during any particular radiation therapy treatment session (e.g., a radiation therapy treatment may require multiple sessions of radiation therapy, where each session is typically referred to as a 'fraction'). Further, such images are used to determine the geometric accuracy of patient positioning relative to the radiation head 306.

The intersection of an axis 316 with the center of the beam 310, produced by the radiation head 306, is usually referred to as the isocenter. The patient table 304 may be motorized so the patient 302 can be positioned with the tumor site at or close to the isocenter 314. For instance, the patient table 304 may change positions relative to one or more other components of the linear accelerator, such as to elevate, change the longitudinal position, or the latitudinal position of the patient 302 relative to a therapeutic radiation source located in the radiation head 306.

In some example embodiments, the linear accelerator may be integrated with the image acquisition device 170 (shown in FIG. 1), such as a magnetic resonance imaging device, as a single apparatus (e.g., an MRI-Linac).

Figure 4:
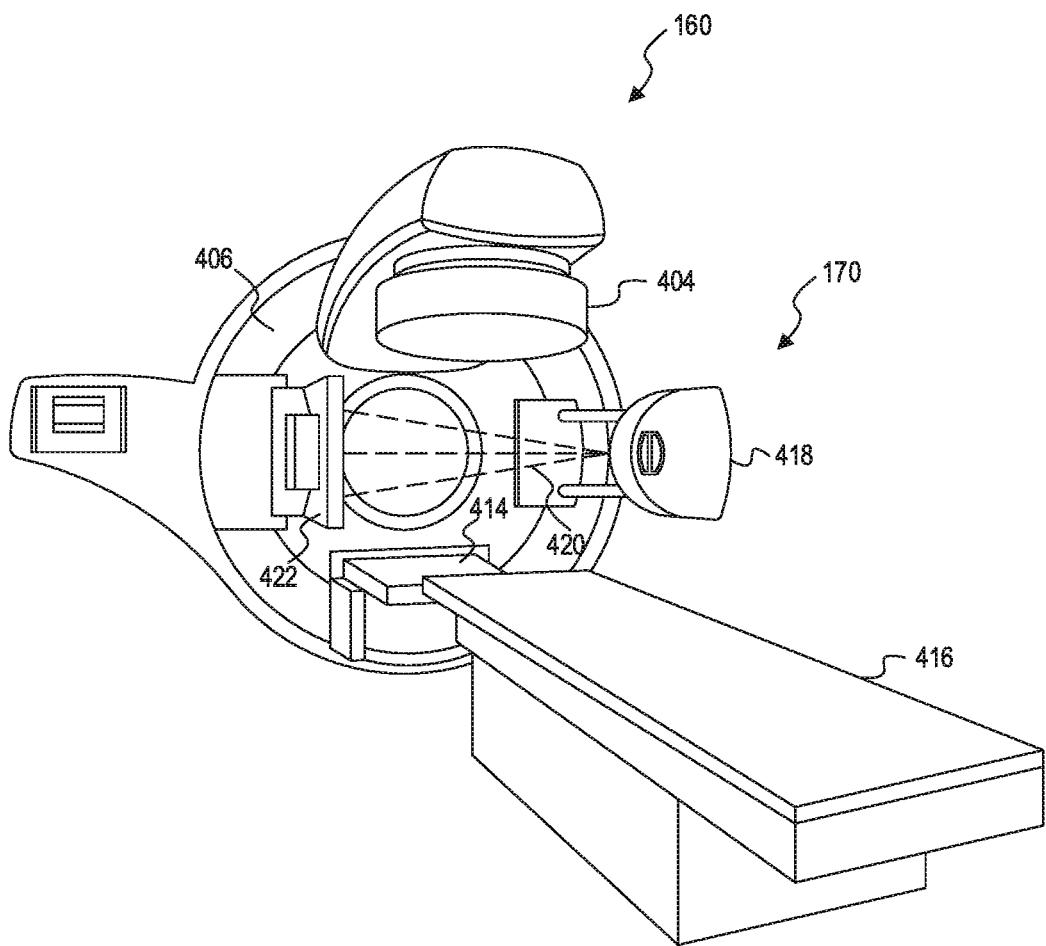
FIG. 4 illustrates an example of a combined radiation therapy device and an imaging device, such as a computed tomography (CT) imaging device, which may be used in the adaptive radiotherapy system of FIG. 1.

FIG. 4 illustrates an exemplary system that can include a combined radiation therapy device 160 and an image acquisition device 170, such as can include a computed tomography (CT) imaging device. The CT imaging device can include an imaging X-ray source 418, such as providing X-ray energy in a kiloelectron-Volt (keV) energy range or a megaelectron-Volt (MeV) range. The imaging X-ray source 418 provides a fan-shaped and/or a conical beam 420 directed to an imaging detector 422, such as a flat panel detector. The radiation therapy device 160 can be similar to the device 160 described in relation to FIG. 3, such as including a radiation head 404, a gantry 406, a patient table 416, and a flat panel scintillator 414. As in the examples of FIG. 3 and FIG. 5, the radiation therapy device 160 can be coupled to, or can include, a high-energy accelerator configured to provide a therapeutic radiation beam. The X-ray source 418 can provide a comparatively-lower-energy X-ray diagnostic beam, for imaging.

In the illustrative example of FIG. 4, the radiation head 404 and the X-ray source 418 can be mounted on the same rotating gantry 406, rotationally-separated from each other by 90 degrees. In another example, two or more X-ray sources can be mounted along the circumference of the gantry 406, such as each having its own detector arrangement to provide multiple angles of diagnostic imaging concurrently. Similarly, multiple radiation heads 404 can be provided.

Figure 5:
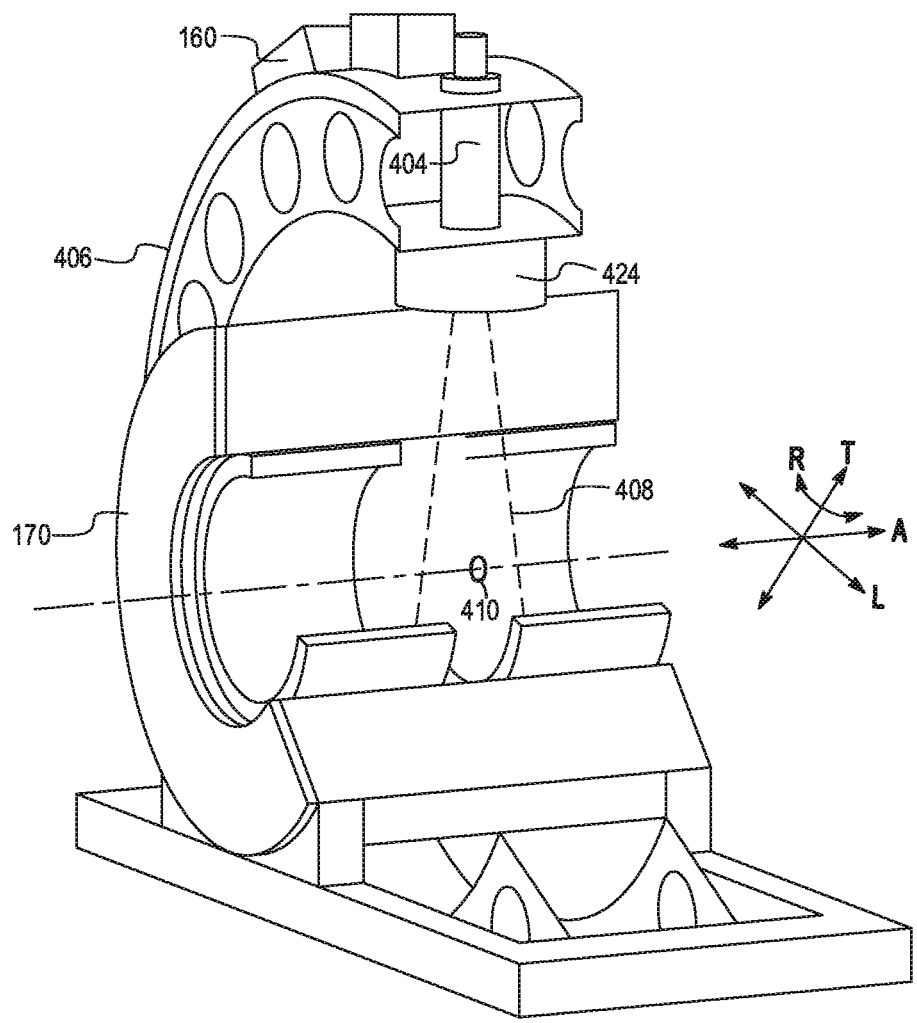
FIG. 5 illustrates another example of a combined radiation therapy device and an imaging device, such as a nuclear magnetic resonance (MR) imaging device, which may be used in the adaptive radiotherapy system of FIG. 1.

FIG. 5 illustrates a partially cut-away view of an exemplary system that can include a combined radiation therapy device 160 and an image acquisition device 170, such as can include a nuclear magnetic resonance (MR) imaging device. The MR imaging device can be arranged to define a "bore" around an axis ("A"), and the radiation therapy device can include a radiation head 404, such as to provide a radiation therapy beam 408 directed to an isocenter 410 within the bore along the axis, A. The radiation head 404 can include a collimator 424, such as to one or more of control, shape, or modulate radiation therapy beam 408 to direct the beam 408 to a therapy locus aligned with a desired target locus within a patient. The patient can be supported by a patient table. The patient table can be positioned along one or more of an axial direction, A, a lateral direction, L, or a transverse direction, T. One or more portions of the radiation therapy device 160 can be mounted on a gantry 406, such as to rotate the radiation head 404 about the axis A.

FIG. 3, FIG. 4, and FIG. 5 illustrate examples including a configuration where a therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a table supporting the patient can be used to align a radiation therapy isocenter with a specified target locus within the patient.

Figure 6:
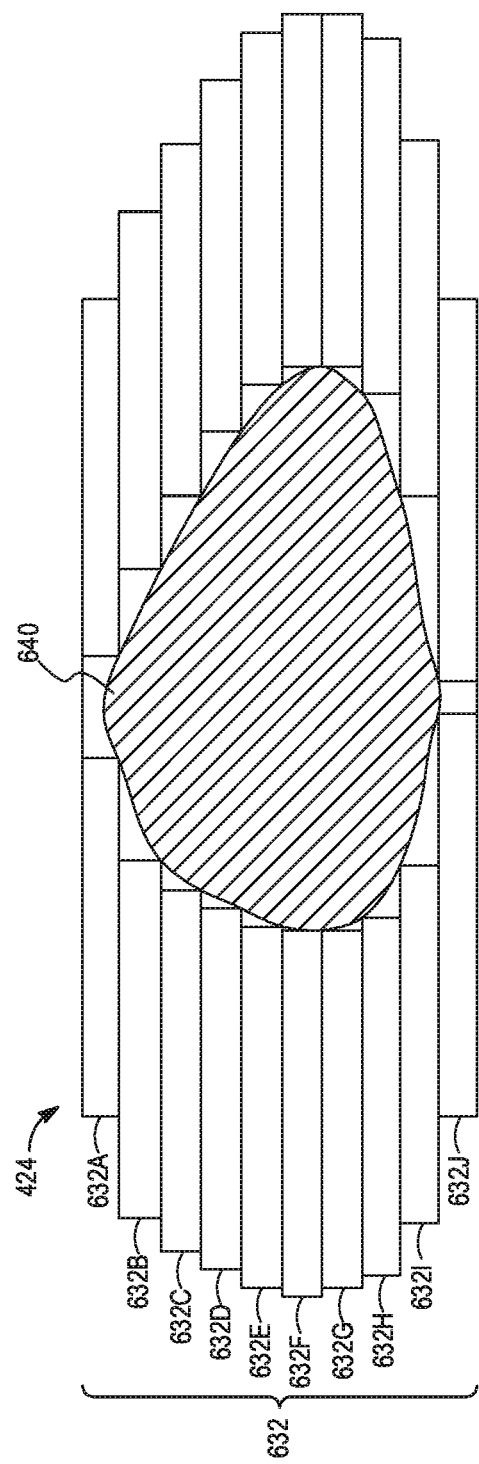
FIG. 6 illustrates an exemplary collimator configuration for shaping, directing, or modulating an intensity of a radiation therapy beam.

FIG. 6 illustrates an exemplary multi-leaf collimator (MLC) 632, for shaping, directing, or modulating an intensity of a radiation therapy beam. In FIG. 6, leaves 632A through 632J can be automatically positioned to define an aperture approximating a tumor 640 cross section or projection. The leaves 632A through 632J can be made of a material specified to attenuate or block the radiation beam in regions other than the aperture, in accordance with the radiation treatment plan. For example, the leaves 632A through 632J can include metallic plates, such as comprising tungsten, with a long axis of the plates oriented parallel to a beam direction, and having ends oriented orthogonally to the beam direction (as shown in the plane of the illustration of FIG. 6). A "state" of the MLC 632 can be adjusted adaptively during a course of radiation therapy, such as to establish a therapy beam that better approximates a shape or location of the tumor 640 or other target locus, as compared to using a static collimator configuration or as compared to using an MLC 632 configuration determined exclusively using an "offline" therapy planning technique. A radiation therapy technique using the MLC 632 to produce a specified radiation dose distribution to a tumor or to specific areas within a tumor can be referred to as Intensity Modulated Radiation Therapy (IMRT).

Figure 7:
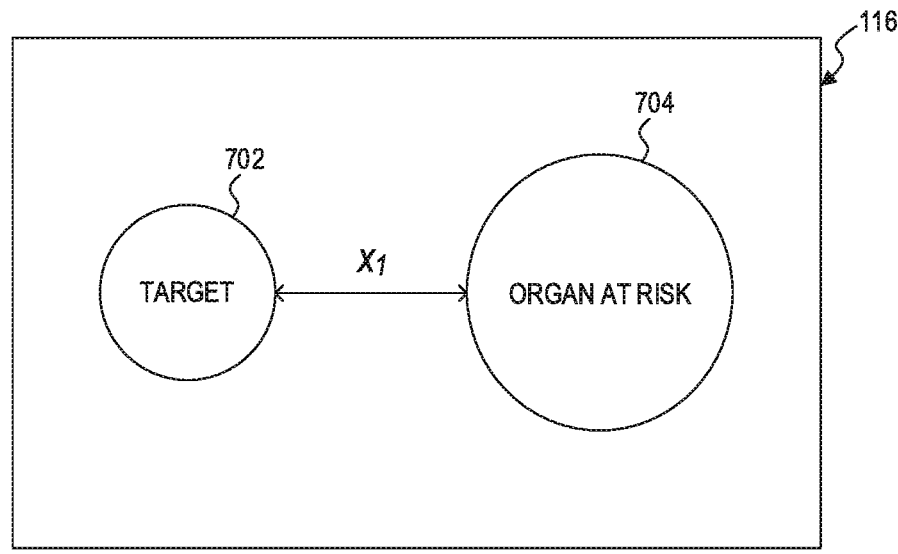
FIGS. 7 and 8 are simplified two-dimensional representations of medical images of a part of a patient's body taken at different times, according to an exemplary embodiment.
Figure 8:
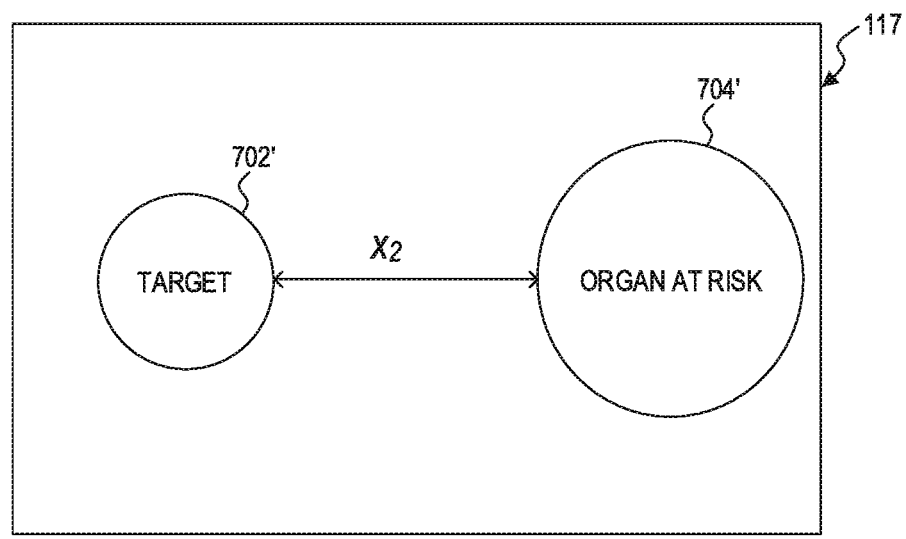

Referring again to FIG. 1, the treatment planning device 110 is configured to modify a treatment plan 126 to compensate for variation of a patient's anatomy. To illustrate how a patient's anatomy can move, FIGS. 7 and 8 are simplified two-dimensional representations of medical images of the same part of a patient's body at different times, according to an exemplary embodiment. As shown in FIG. 7, a first medical image 116 includes a target 702 and an organ at risk (OAR) 704, which are separated by a distance $x_1$. FIG. 8 shows a second medical image 117, which is acquired after the first medical image 116. In the second medical image, the separation between the target 702' and the OAR 704' has increased to a distance $x_2$.

There are many factors that can cause variation of a patient's anatomy. For example, the size of the target 702 can decrease as a result of successful radiation therapy treatment. Conversely, the size of the target 702 can increase due to growth of a tumor in the time since the first medical image 116 was acquired. A change in the patient's weight, or the filling or emptying of organs such as the bladder or bowel may also cause variation of the patient's anatomy. It will be appreciated that the variation of the patient's anatomy may, of course, be more complicated than illustrated in FIGS. 7 and 8, and may involve changes in the size, shape and/or position of a target 702 and/or one or more OARs 704.

In adaptive radiotherapy, a DVF (DVF) can be used to modify a treatment plan to compensate for variation of a patient's anatomy. The DVF is a 3D array whose elements are vectors. Each vector in the DVF defines a geometric transformation to map a voxel in a first medical image to a corresponding voxel in a second medical image. For example, a DVF can map each voxel in a planning image to a corresponding voxel in an image acquired shortly before (or during) a radiation therapy treatment session.

FIG. 9 shows a DVF 121 for mapping the first medical image 116 of FIG. 7 to the second medical image 117 of FIG. 8. The DVF 121 comprises a plurality of vectors 906. The vectors 906 are illustrated by arrows, the size and direction of which represent a geometric translation that maps a voxel in the first medical image 116 to a corresponding voxel in the second medical image 117. To assist in understanding the DVF 121, FIG. 9 also shows the target 702 and OAR 704 in their positions when the first medical image 116 was acquired, and the target 702' and OAR 704' in their positions when the second medical image 117 was acquired. In the example shown in FIG. 9, the left side of the DVF 121 comprises vectors that cause voxels to remain stationary, thus mapping the target from 702 to 702'. The right side of the DVF 121 comprises vectors that cause voxels to be translated parallel to the positive direction of the x axis, thus mapping the OAR from 704 to 704'.

It will be appreciated that FIG. 9 shows a simple two-dimensional example of a DVF 121. In practice, the DVF 121 may be a two, three or four-dimensional array, whose vectors may define any type of geometric transformation that maps the first medical image 116 to the second medical image 117. The geometric transformations defined by the vectors may include any combination of a translation, a rotation and/or a volumetric change (e.g., expansion or contraction).

As noted above, the DVF 121 is an array whose elements are vectors that define a geometric transformation to map a voxel in a first medical image 116 to a corresponding voxel in a second medical image 117. The DVF 121 can transform the dose distribution that is defined by a treatment plan 126, in order to compensate for variation of a patient's anatomy that has occurred during the period of time between acquisition of the first and second medical images. To put this another way, the same geometric transformations that allow the first medical image 116 to be mapped to the second medical image 117 also allow the dose distribution defined by the treatment plan 126 to be mapped to a new dose distribution that takes into account the variation of the patient's anatomy.

FIG. 10 illustrates how a DVF 121 can be used to transform a dose distribution. FIG. 10 is a graph of dose against distance, in which distance is measured from the center of the target 702. For the sake of simplicity, only the positive horizontal axis is shown. A dose distribution defines the dose of radiation that is to be delivered to each point in a patient's body. In practice, a dose distribution defines the dose in three spatial dimensions, but only one spatial dimension is shown in FIG. 10. The dose distribution defined by a treatment plan to treat the target 702 of FIG. 7 is denoted by reference numeral 1000. The dose distribution after the dose distribution has been transformed by the DVF 121 of FIG. 9 is denoted by the reference numeral 1010. In the example shown in FIG. 10, the DVF 121 causes the dose distribution 1010 to be spread over a greater volume than the original dose distribution 1000, which has the disadvantage of increasing the exposure to radiation of healthy tissue surrounding the target 702'. Furthermore, because the total radiation dose prescribed by the treatment plan is constant, spreading the dose distribution 1010 over a greater volume has the further disadvantage of reducing the dose applied to the target 702', which reduces the efficacy of the treatment plan.

The treatment planning device 110 is configured to modify a treatment plan 126 to compensate for variation of a patient's anatomy, while avoiding the dose distribution being spread over a greater volume. This is achieved by modifying the DVF 121 to reduce the magnitude of vectors that cause voxels to move away from the target 702. The modified DVF 124 may be used to transform a dose distribution 1000. The transformed dose distribution may be used to generate a new treatment plan 129. Modifying the DVF 121 in this manner prevents the dose distribution being spread over a greater volume, but still compensates for variation in the patient's anatomy. The new treatment plan 129 may thus ensure that the target 702 receives the prescribed dose, and may reduce the exposure to radiation of healthy tissue surrounding the target 702.

Figure 11:
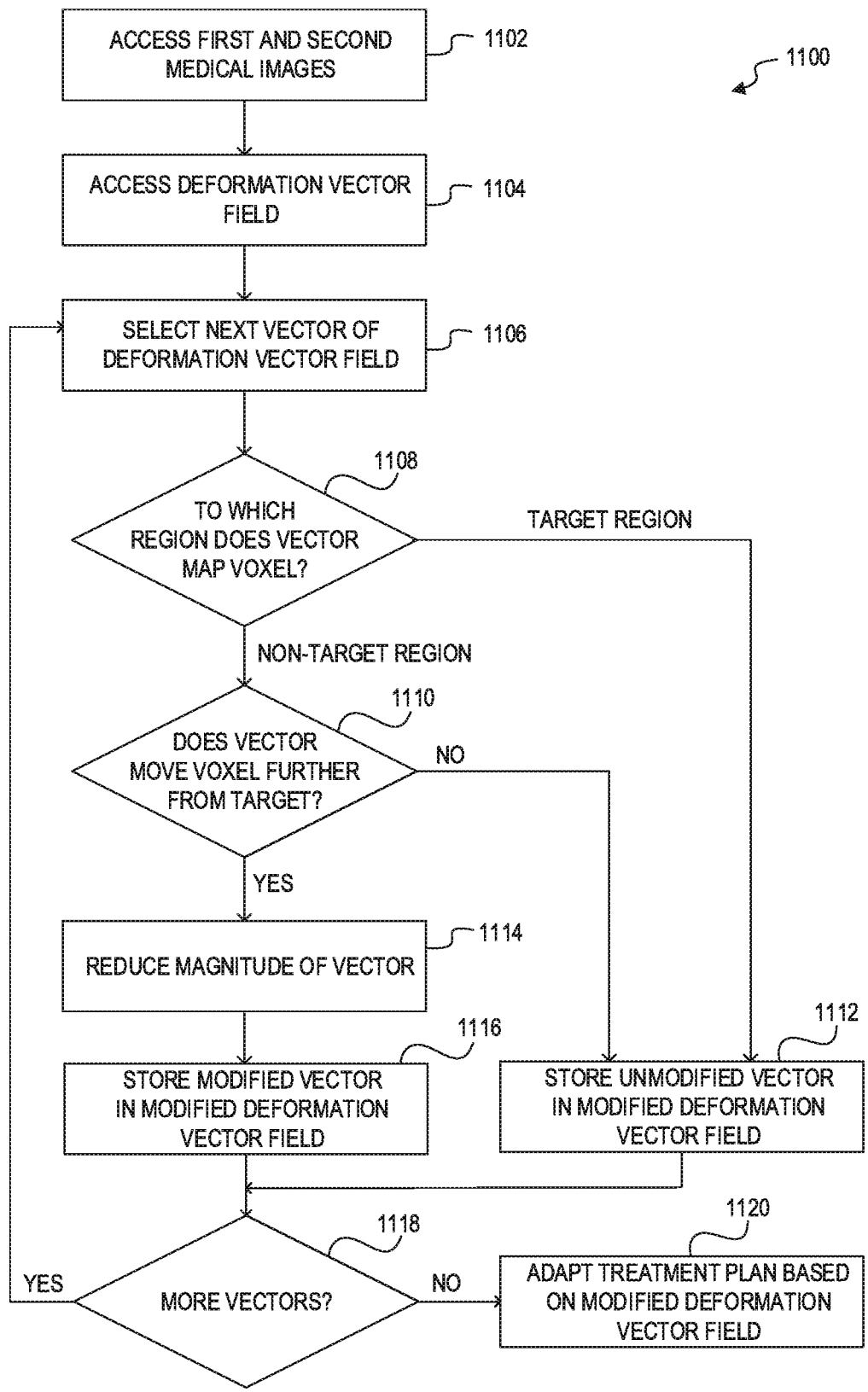
FIG. 11 is a flow diagram of an exemplary method of adaptive radiotherapy.

An exemplary method of adaptive radiotherapy, which may be performed using the treatment planning device 110, will now be described with reference to FIG. 11.

The method 1100 begins at step 1102, in which the treatment planning device 110 accesses a first medical image 116 and a second medical image 117. The first and second medical images 116, 117 each represent a region of interest of a patient at different times. More specifically, the first and second medical images 116, 117 both depict substantially the same part of the patient's anatomy, but the first medical image 116 is acquired at an earlier time than the second medical image 117. For example, the first medical image 116 may be a planning image acquired several days before a radiation therapy treatment session, while the second medical image 117 may be acquired shortly before (or during) a radiation therapy treatment session. Accessing 1102 the first and second medical images 116, 117 may include the processor 112 reading the images from the memory device

111. Alternatively or additionally, accessing 1102 the first and second medical images 116, 117 may include the processor 112 retrieving either or both images from the database 140, hospital database 142, oncology information system 150 and/or image acquisition device 170.

The first and second medical images 116, 117 may be two, three or four-dimensional images. Each medical image 116, 117 is composed of a plurality of elements, known as voxels. Each voxel represents the intensity of an image 116, 117 at a particular point in space. The first and second medical images may 116, 117 may have been acquired by any suitable imaging modality. For example, the first medical image 116 may be a planning image that has been acquired using computed tomography (CT), magnetic resonance imaging (MRI), positron emission tomography (PET), ultrasound or single photon emission computerized tomography (SPECT). As another example, the first medical image 116 may be a planning image that has been generated by fusing using images acquired using two or more different imaging modalities. The second medical image 117 may have been acquired using the same imaging modality as the first medical image 116, or using a different imaging modality. For example, the second medical image 117 may be acquired when the patient is positioned on a radiation therapy device 160 using cone-beam CT (CBCT), ultrasound, MRI, portal imaging, CT-on-rails or on-board kV imaging. In some cases, fiducial markers can be implanted in the patient to help with visibility of the target. Some technologies have been developed that do not use imaging at all, but rely on the imageless detection of the position of active fiducials, for example by implanting radiofrequency (RF) beacons. For generality, the term "image" as used herein includes positional information of fiducials, or any data collected about the patient's interfractional state, such as target or OAR positions, rotations or deformations, blood pressure, heart rate, weight, deformation, etc.

The first and second medical images 116, 117 are each segmented into a target region and at least one non-target region. In an example. The first and second medical images 116, 117 are each segmented into one or more target regions and one or more non-target regions. Segmentation generally refers to a process of assigning labels to voxels in an image in order to denote what those voxels represent. Thus, the target region includes a plurality of voxels that are labelled as a target 702 to be treated by exposure to radiation. Each non-target region includes a plurality of voxels that are labelled as something other than the target 702. For example, a non-target region may include voxels that that are labelled as an organ at risk 704. Each medical image 116, 117 may include one or more organs at risk. As another example, a non-target region may include voxels that are labelled as background voxels, i.e. voxels that do not represent the body of the patient. The first and second medical images 116, 117 may have been segmented manually (e.g., by a physician, dosimetrist, or health care worker) or automatically (e.g., using a program such as the Atlas-based auto-segmentation software, ABAS®, manufactured by Elekta AB of Stockholm, Sweden). The first and second medical images 116, 117 are generally segmented before they are accessed at step 1102, but may be segmented as part of step 1102.

At step 1104, the treatment planning device 110 accesses a DVF 121. The DVF 121 includes a plurality of vectors, each of which defines a geometric transformation to map a respective voxel in the first medical image 116 to a corresponding voxel in the second medical image 117. Accessing the DVF 121 in step 1104 may include the processor 112 reading the DVF from the memory device 111, or retrieving the DVF 121 from the database 140, hospital database 142 and/or oncology information system 150. Alternatively, accessing the DVF 121 may include generating the DVF from the first and second medical images 116, 117. The DVF 121 can be generated by any suitable method. For example, the DVF 121 can be generated using a deformable image registration algorithm. The present disclosure is not limited to any particular method of generating a DVF 121.

Steps 1106 to 1118 define an iterative process for generating a modified DVF 124 based upon the original DVF 121 that was accessed at step 1104. At step 1106, a vector of the DVF 121 is selected.

At step 1108, the selected vector is analyzed to determine whether it maps a voxel in the first medical image 116 to the target region or a non-target region of the second medical image 117. For example, the labels in the segmented second medical image 117 can be used to determine whether the vector maps to the target region or a non-target region. When it is determined that the selected vector maps the voxel to the target region of the second medical image 117, the method proceeds to step 1112. Alternatively, when it is determined that the selected vector maps the voxel to a non-target region of the second medical image 117, the method proceeds to step 1110.

At step 1110, the selected vector is analyzed to determine whether it causes the distance between a voxel and the target region to increase. When it is determined that the selected vector causes the distance between the voxel and the target region to increase, the method proceeds to step 1114. Alternatively, when it is determined that the selected vector causes the distance between the voxel and the target region to decrease, or causes no change to the distance between the voxel and the target region, the method proceeds to step 1112.

Step 1110 may be implemented by calculating a distance transform from the boundary of the target 702, 702' in the first and second medical images 116, 117. A distance transform is an array having the same resolution as an image from which it is derived, and in which the value of each element of the array is the shortest distance (measured in voxels) from the corresponding voxel of the image to the closest point on a specified boundary in the image. The distance transforms of the first and second medical images 116, 117 can be compared to determine whether the selected vector maps a voxel in the first medical image 116 to a voxel that is further away from the boundary of the target 702' in the second medical image 117. Distance transforms provide a computationally efficient way of determining how the selected vector affects the distance of a voxel from the target region. The distance transforms only need to be calculated once, and do not need to be recalculated during each iteration of step 1110. Other ways of implementing step 1110 will be apparent to those skilled in art, and are within the scope of the claims.

At step 1112, the selected vector is stored, without being modified, in the modified DVF 124. The selected vector is not modified because it does not cause the dose to spread away from the target 702 when the modified DVF 124 is used to transform the dose distribution. That is, the selected vector is not modified because its effect is to transform the dose distribution to compensate for variation of the target 702, without causing the OAR 704 to be exposed to a greater dose of radiation.

At step 1114, the magnitude of the selected vector is reduced. The magnitude can be reduced by multiplying the selected vector with a scalar having a value between zero and one. Alternatively, the magnitude can be reduced by setting all of the components of the selected vector to zero. The magnitude of the selected vector is reduced because the vector would otherwise cause the dose to spread away from the target 702 when the modified DVF 124 is used to transform the dose distribution. By reducing the magnitude of the selected vector, the spreading of the dose distribution can be reduced or avoided. This can avoid the OAR 704 being exposed to a greater dose of radiation than prescribed by the treatment plan.

The amount by which the magnitude of the selected vector is reduced may be selected to satisfy one or more criteria. For example, the magnitude of the selected vector may be reduced by an amount that ensures that the gradient (i.e., the derivative of dose with respect to distance) of a transformed dose distribution generated using the modified DVF 124 is the same as that of the original dose distribution. As another example, the magnitude of the selected vector may be reduced by an amount that ensures that the dose in the transformed dose distribution is a continuous function of distance. It will be appreciated that satisfying these criteria may involve the magnitudes of different vectors being reduced by different amounts.

At step 1116, the modified vector generated at step 1114 is stored in the modified DVF 124.

The modified DVF 124 may be generated by creating a new data structure in the memory device 111, and populating that data structure by multiple iterations of steps 1112 and 1116. Alternatively, the modified DVF may be generated by modifying the original DVF 121. In the latter case, the values of vectors in the original DVF 121 may be overwritten at step 1116, while the existing values of vectors in the original DVF 121 may be left unmodified by step 1112.

At step 1118, a determination is made as to whether the DVF 121 has any more vectors to be processed. When it is determined that the DVF 121 has at least one more vector to be processed by steps 1106 to 1116, the method returns to step 1106. Alternatively, when it is determined that the DVF 121 has no more vectors to be processed, the method proceeds to step 1120.

At step 1120, the modified DVF 124 may be used to adapt a treatment plan. Step 1120 may be implemented by using the modified DVF 124 to transform the dose distribution defined by an original treatment plan 126. The original treatment plan 126 may have been generated by commercially-available treatment planning software (such as the Monaco® software manufactured by Elekta), and may include a dose distribution prescribed by a physician. Transforming the dose distribution by the modified DVF 124 results in a transformed dose distribution that compensates for variation of the patient's anatomy. The transformed dose distribution may then be used to generate a new treatment plan 129, which also compensates for variation of the patient's anatomy. The new treatment plan 129 can be generated from the transformed dose distribution using the inverse planning capabilities of commercially-available treatment plan optimization software, such as the Monaco® software manufactured by Elekta AB. The treatment plan optimization software may be a component of the treatment planning module 128 that is stored in the memory device 111 of the treatment planning device 110. The new treatment plan 129 may be used by the radiation therapy device 160 to perform a radiation therapy treatment session.

Figure 12:
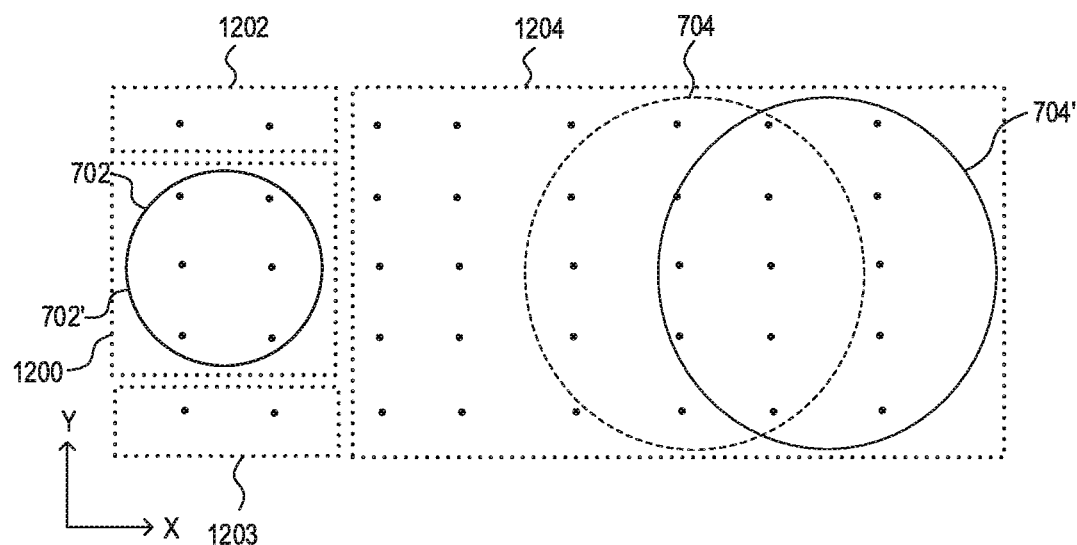
FIG. 12 illustrates a exemplary modified deformation vector field generated by the method of FIG. 11.

FIG. 12 shows the modified DVF 124 that is generated by performing the method 1100 upon the DVF 121 shown in FIG. 9. The vectors in region 1200 map voxels in the first medical image 116 to the target region of the second medical image 117. Hence, the vectors in region 1200 of the modified DVF 124 are identical to the corresponding vectors of the original DVF 121. Each vector in regions 1202 and 1203 cause no change to the distance between a voxel and the target region. Hence, the vectors in regions 1202 and 1203 of the modified DVF 124 are identical to the corresponding vectors of the original DVF 121. Each vector in region 1204 causes the distance between a respective voxel and the target region to increase. Hence, the magnitude of each vector in region 1204 of the modified DVF 124 is less than that of the corresponding vector of the original DVF 121.

Figure 13:
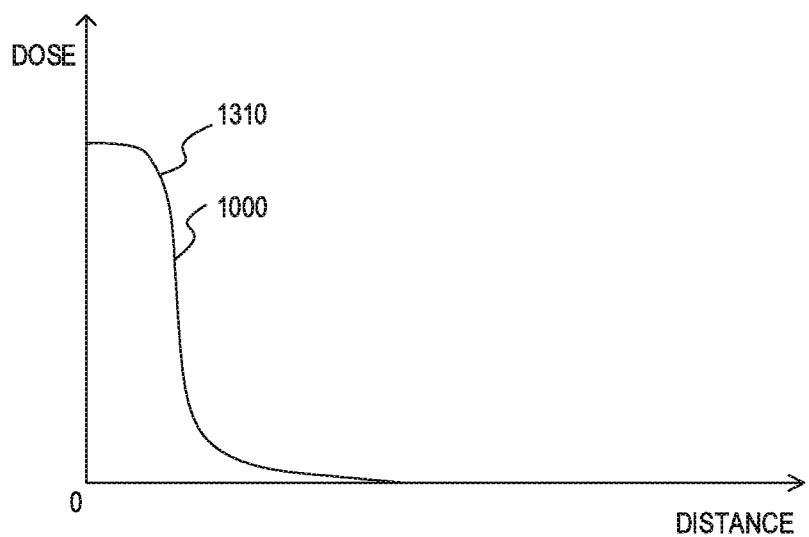
FIG. 13 illustrates exemplary dose distributions before and after transformation by the deformation vector field of FIG. 12.

FIG. 13 illustrates the use of the modified DVF 124 to transform a dose distribution. As with FIG. 10, FIG. 13 is a graph of dose against distance, in which distance is measured from the center of the target 702, and in which only one spatial dimension and only the positive horizontal axis are shown. The dose distribution defined by the original treatment plan 126 to treat the target 702 of FIG. 7 is denoted by reference numeral 1000. The dose distribution after the dose distribution has been transformed by the modified DVF 124 of FIG. 12 is denoted by the reference numeral 1310. In the example shown in FIG. 13, the modified DVF 124 leaves the dose distribution unchanged. Hence, the modified dose distribution 1310 does not increase the exposure to radiation of healthy tissue surrounding the target 702', nor does it reduce the dose applied to the target 702'.

Figure 14:
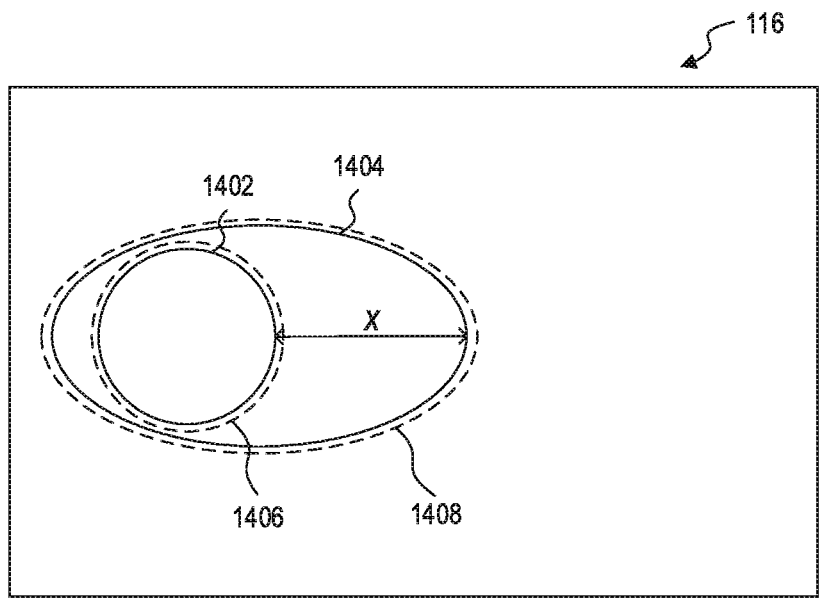
FIGS. 14 and 15 are simplified two-dimensional representations of medical images of a part of a patient's body taken at different times, according to an exemplary embodiment.
Figure 15:
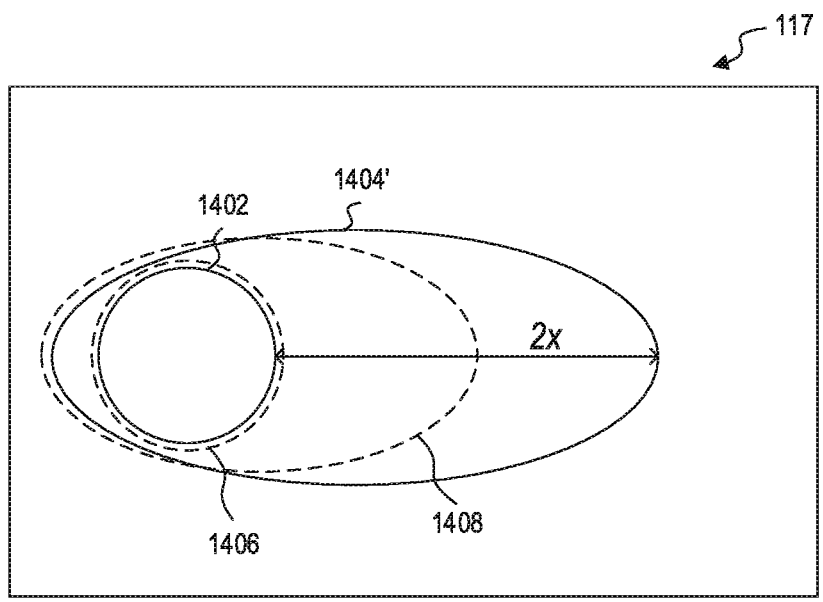

FIGS. 14 and 15 are simplified two-dimensional representations of medical images of the same part of a patient's body at different times, according to an exemplary embodiment. As shown in FIG. 14, a first medical image 116 includes a first target 1402 and a second target 1404. The first target 1402 may be positioned within, or may overlap with a portion of, second target 1404. An edge portion of the first target 1402 and an edge portion of the second target 1404 are separated by a distance x. First target 1402 and second target 1404 have margins 1406 and 1408, respectively, spaced a distance from the respective target. For example, the margins 1406 and 1408 may be spaced 1 cm from respective targets 1402 and 1404. FIG. 15 shows a second medical image 117, which is acquired a time period after the first medical image 116. In the second medical image 117, second target 1404' has increased in size, while first target 1402 remains the same size as in first medical image 116. In FIG. 15, the separation between the edge portion of the first target 1402 and the edge portion of the second target 1404' has increased to distance 2x.

In some embodiments, user may wish to deliver different doses of radiation to first target 1402 and second target 1404. For example, a user may wish to deliver 70 Gy to first target 1402 and 60 Gy to second target 1404. However, the original treatment plan 126, which may have been generated using first medical image 116, may no longer be appropriate due to the expansion of second target 1404'. Treatment planning device 110 may compensate for this expansion by generating a new treatment plan 129.

In some embodiments, treatment planning device 110 may compensate for movement of first target 1402 and second target 1404' using, for example, steps of method 1100. Device 110 may generate DVF 121, process the DVF 121 to generate modified DVF 124, and execute new treatment plan 129 using modified DVF 124. During DVF processing, DVF vectors corresponding to voxels which move further away from first target 1402 and/or second target 1404' are reduced in magnitude, thus minimizing delivery of radiation to surrounding tissues.

Additionally, in some embodiments, modified DVF 124 may be post-processed by treatment planning device 110 to compensate for the increased size of second target 1404'.

During post-processing, all or a fraction of the vectors in modified DVF 124 are scaled in magnitude to compensate for the increased size of second target 1404'. An example of a post-processing implementation is described below in the discussion of FIG. 16. The dose distribution resulting from the application of the post-processed DVF maintains the same gradient across the body of second target 1404' as the dose distribution resulting from the application of the modified DVF 124, allowing delivery of the target dose (e.g. 60 Gy) to the entire expanded volume of second target 1404'.

In one embodiment, vectors within modified DVF 124 corresponding to voxels within first target 1402 may remain unchanged during post-processing. As a result, the post-processed DVF will compensate for any movement of first target 1402 between first medical image 116 and second medical image 117, but will otherwise deliver the same radiation dose to first target 1402. This is due to the fact that the size of first target 1402 did not change between the time first medical image 116 was taken and the time second medical image 117 was taken. Once post-processing is complete, the post-processed DVF may be applied to transform a dose distribution, and the transformed dose distribution may be used to generate new treatment plan 129.

Alternatively, if the second target 1404' decreases in size, modified DVF 124 may be post-processed to cause delivery of a comparably decreased radiation dose to second target 1404', wherein the gradient of the dose distribution resulting from the application of the post-processed DVF across second target 1404' is the same as the dose distribution resulting from the application of the in modified DVF 124. One of skill in the art will recognize that treatment planning device 110 may perform post-processing of the modified DVF 124 to compensate for increased or decreased target size when there is only a single target. That is, treatment planning device 110 may identify a single target, generate a modified DVF 124 to compensate for movement of the single target between first medical image 116 and second medical image 117, and post-process the DVF 124 to compensate for increases and/or decreases in size of the single target.

Figure 16:
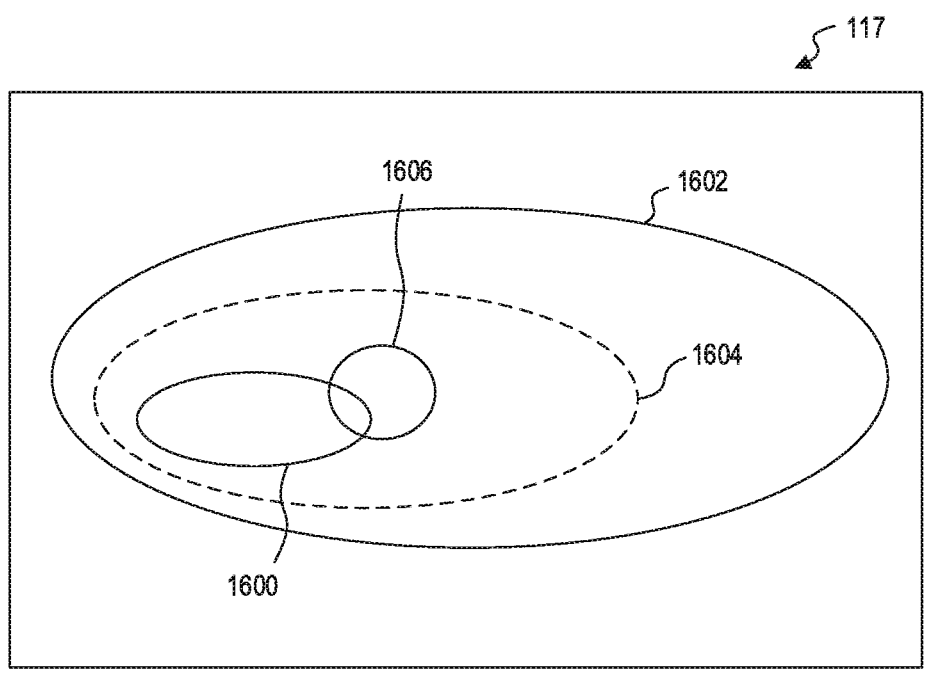
FIG. 16 illustrates post-processed DVF application based on a DVF to map the simplified two-dimensional representation of a medical image of a part7 illustrates dose distributions before and after transformation by the DVF of a patient's body.

FIG. 16. Illustrates an exemplary post-processed DVF distribution based on a simplified two-dimensional representation of a second medical image 117. Second medical image 117 may be an image of a part of a patient's anatomy and may be acquired shortly before (or during) a radiation therapy treatment session. Second medical image 117 depicts a target 1600, which may have changed in size, shape, and/or location between the time when first medical image 116 was taken and the time when second medical image 117 was taken. According to one example, target 1600 may have increased in size. Because DVF 121 was generated according to the prior, first medical image, modified DVF 124 may require post-processing to generate a post-processed DVF to compensate for the change of target 1600.

FIG. 16 depicts target 1600, as well as OAR 1606 and at least a portion of the patient's skin 1602. In the exemplary embodiment depicted in FIG. 16, target 1600 and OAR 1606 may overlap. However, one of skill in the art will understand that this embodiment is merely exemplary, and that the implementation described with reference to FIG. 16 may be applied to anatomies in which the target and OAR do not overlap, or in which there is no OAR in proximity to the target.

During post-processing of modified DVF 124, treatment planning device 110 may determine the location of contour 1604, which represents a contour between target 1600 and skin 1602; in some examples, the contour can be a half-way contour, that is, contour 1604 is a line of voxels in second medical image 117 each having a distance transform to target 1600 equal to the distance transform to the skin 1602. The post-processed DVF may be generated by modifying all or a fraction of the vectors within modified DVF 124 and storing the vectors within the post-processed DVF. The vector processing techniques may vary depending on the location of the corresponding voxel within second medical image 117.

According to some embodiments, DVF vectors mapping to voxels within target 1600 (the "first group of voxels") may be accessed from modified DVF 124 and stored in the unmodified, post-processed DVF. That is, vectors mapping to the first group of voxels are the same in the modified DVF 124 and in the post-processed DVF.

For each voxel in second medical image 117 within contour 1604 and outside target 1600 and OAR 1606 (represented as shaded area in FIG. 16; the "second group of voxels"), device 110 may determine the location of the nearest voxel within target 1600, as well as the magnitude of the nearest voxel's DVF vector. Because the DVF vectors for the first group of voxels are the same in the modified DVF 124 and in the post-processed DVF, these vector magnitudes may be accessed from one or both of the modified DVF 124 and in the post-processed DVF. Device 110 then generates a modified vector for each of the second group of voxels equal to the magnitude of the nearest target voxel's DVF vector, and stores each modified vector in the post-processed DVF. In this way, the second group of voxels is radially constant.

For each voxel outside contour 1604 (the "third group of voxels"), device 110 may interpolate a vector between contour 1604 and skin 1602, and store the interpolated vector within the post-processed DVF. As a result, there is no crushing of isodose lines near contour 1604 or skin 1602.

For each voxel (the "fourth group of voxels") in regions in second medical image 117 in which target 1600 and OAR 1606 overlap, each voxel can be treated as a target.

After post-processing of the DVF is completed, the post-processed DVF may be applied to a treatment dose, which may be used to generate a treatment plan. Because the post-processed DVF corrects for changes in target size and for target movement, the treatment plan may accurately deliver the proper radiation dose to the entire target volume with minimized radiation delivery to surrounding tissues and to the OAR. One of skill in the art will recognize that the DVF post-processing implementation of FIG. 16 is merely exemplary, and that other implementations may be used with the present disclosure.

The present disclosure also relates to a system for performing the operations described herein. This system may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in the embodiments illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of the claims.

The present disclosure may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

It will be apparent that modifications and variations are possible without departing from the scope of appended claims. As various changes could be made in the above constructions, products, and methods without departing from the scope of the claims, it is intended that all matter contained in the above description and shown in the accompanying drawings shall be interpreted as illustrative and not in a limiting sense.

What is claimed is:

1. A processor-implemented method for generating a modified deformation vector field from a deformation vector field that is for use in adaptive radiotherapy and that utilizes first interfractional patient state data and second interfractional patient state data, the method comprising:
   identifying a first vector in the deformation vector field that maps first data in the first interfractional patient state data to first data in a non-target region in the second interfractional patient state data,
   modifying a magnitude of the first vector in response to determining that the first vector increases a distance between the mapped data and a target region, and
   storing the modified first vector in the modified deformation vector field.

2. The method of claim 1, further comprising:
   identifying a second vector in the deformation vector field that maps second data in the first interfractional patient state data to second data in a non-target region in the second interfractional patient state data;
   determining whether the second vector causes a distance between the second mapped data and the target region to decrease, or causes no change to the distance between the second mapped data and the target region; and
   storing the second vector in the modified deformation vector field when it is determined that the second vector causes the distance between the second mapped data and the target region to decrease, or causes no change to the distance between the second mapped data and the target region.

3. The method of claim 1, further comprising:
   identifying a third vector in the deformation vector field, wherein the third vector maps third data in the first interfractional patient state data to third data in the target region in the second interfractional patient state data; and
   storing the third vector in the modified deformation vector field.

4. The method of claim 1, further including adapting a treatment plan based upon the modified deformation vector field.

5. The method of claim 4, wherein the treatment plan comprises a dose distribution, and wherein adapting the treatment plan includes:
   transforming the dose distribution with the modified deformation vector field; and
   generating a new treatment plan based on the transformed dose distribution.

6. The method of claim 5, wherein the method further includes:
   applying therapeutic radiation to a patient in accordance with the new treatment plan.

7. The method of claim 1, wherein determining that the first vector increases a distance between the mapped data and the target region includes:
   calculating a distance transform from a boundary of the target region in the first interfractional patient state data;
   calculating a distance transform from a boundary of the target region in the second interfractional patient state data; and
   comparing the distance transforms to determine whether the first vector maps data in the first interfractional patient state data to data that is further away from the boundary of the target region in the second interfractional patient state data.

8. The method of claim 1, further including postprocessing the modified deformation vector field to reduce discontinuities in the modified deformation vector field and to generate a post-processed deformation vector field.

9. The method of claim 8, wherein the first interfractional patient state data is a first medical image, and wherein the second interfractional patient state data is a second medical image, and wherein post-processing the modified deformation vector field to generate a post-processed deformation vector field includes:
   identifying, in the second medical image, a contour between the target region and a patient's skin;
   adjusting a first group of vectors from the modified deformation vector field corresponding to a first group of voxels outside of the contour and within the patient's skin;
   identifying a second group of vectors from the modified deformation vector field corresponding to a second group of voxels within the contour; and
   storing the adjusted first group of vectors in the modified deformation vector field and the unadjusted second group of vectors in the modified deformation vector field to provide a post-processed deformation vector field.

10. The method of claim 9, wherein adjusting the first group of vectors includes interpolating each vector in the first group of vectors between the contour and the skin to provide a post-processed deformation vector field where vectors in the first group continuously change from modified deformation vector field vectors near the contour to unmodified deformation vector field vectors near the patient's skin.

11. A treatment planning system comprising:
    radiation therapy control circuitry that utilizes data from first interfractional patient state data and second interfractional patient state data and is configured to:
    generate a modified deformation vector field from a deformation vector field by:
      identifying a first vector in the deformation vector field that maps first data in the first interfractional patient state data to first data in a non-target region in the second interfractional patient state data, modifying a magnitude of the first vector in response to determining that the first vector increases a distance between the mapped data and a target region, and storing the modified first vector in the modified deformation vector field.

12. The treatment planning system of claim 11, wherein generating the modified deformation vector field further includes:

identifying a second vector in the deformation vector field that maps second data in the first interfractional patient state data to second interfractional patient state data in a non-target region in the second interfractional patient state data;

determining whether the second vector causes a distance between the second mapped data and the target region to decrease, or causes no change to the distance between the second mapped data and the target region; and storing the second vector in the modified deformation vector field when it is determined that the second vector causes the distance between the second mapped data and the target region to decrease, or causes no change to the distance between the second mapped data and the target region.

13. The treatment planning system of claim 11, wherein generating the modified deformation vector field further includes:

identifying a third vector in the deformation vector field, wherein the third vector maps third data in the first interfractional patient state data to third data in the target region in the second interfractional patient state data; and storing the third vector in the modified deformation vector field.

14. The treatment planning system of claim 11, wherein the radiation therapy control circuitry is further configured to:

adapt a treatment plan based upon the modified deformation vector field.

15. The treatment planning system of claim 14, wherein the treatment plan comprises a dose distribution, and wherein the radiation therapy control circuitry is configured to adapt the treatment plan by:

transforming the dose distribution with the modified deformation vector field; and generating a new treatment plan based on the transformed dose distribution.

16. The treatment planning system of claim 15, further comprising a radiation therapy device to receive the new treatment plan and to apply therapeutic radiation to the patient in accordance with the new treatment plan.

17. The treatment planning system of claim 11, wherein determining that the first vector increases a distance between the mapped data and the target region includes:

calculating a distance transform from a boundary of the target region in the first interfractional patient state data;

calculating a distance transform from a boundary of the target region in the second interfractional patient state data; and comparing the distance transforms to determine whether the first vector maps data in the first interfractional patient state data to data that is further away from the boundary of the target region in the second interfractional patient state data.

18. The treatment planning system of claim 11, wherein the radiation therapy control circuitry is configured to generate a modified deformation vector field from a deformation vector field by:

postprocessing the modified deformation vector field to reduce discontinuities in the modified deformation vector field and to generate a post-processed deformation vector field.

19. The treatment planning system of claim 18, wherein the first interfractional patient state data is a first medical image, wherein the second interfractional patient state data is a second medical image, and wherein post-processing the modified deformation vector field to generate a post-processed deformation vector field includes:

identifying, in the second medical image, a contour between the target region and a patient's skin;

adjusting a first group of vectors from the modified deformation vector field corresponding to a first group of voxels outside of the contour and within the patient's skin;

identifying a second group of vectors from the modified deformation vector field corresponding to a second group of voxels within the contour; and storing the adjusted first group of vectors in the modified deformation vector field and the unadjusted second group of vectors in the modified deformation vector field to provide a post-processed deformation vector field.

20. The treatment planning system of claim 19, wherein adjusting the first group of vectors includes interpolating each vector in the first group of vectors between the contour and the skin to provide a post-processed deformation vector field where vectors in the first group continuously change from modified deformation vector field vectors near the contour to unmodified deformation vector field vectors near the patient's skin.

21. A tangible, non-transitory, computer-readable medium comprising instructions for generating a modified deformation vector field from a deformation vector field that is for use in adaptive radiotherapy and that utilizes first interfractional patient state data and second interfractional patient state data that, when executed by a processor, direct the processor to:

identify a first vector in the deformation vector field that maps first data in the first interfractional patient state data to first data in a non-target region in the second interfractional patient state data;

modify a magnitude of the first vector in response to determining that the first vector increases a distance between the mapped data and a target region; and store the modified first vector in the modified deformation vector field.

22. The tangible, non-transitory, computer-readable medium of claim 21 comprising further instructions that, when executed by the processor, direct the processor to:

identify a second vector in the deformation vector field that maps second data in the first interfractional patient state data to second data in a non-target region in the second interfractional patient state data;

determine whether the second vector causes a distance between the second mapped data and the target region to decrease, or causes no change to the distance between the second mapped data and the target region; and store the second vector in the modified deformation vector field when it is determined that the second vector causes the distance between the second mapped data and the target region to decrease, or causes no change to the distance between the second mapped data and the target region.

23. The tangible, non-transitory, computer-readable medium of claim 22 comprising further instructions that, when executed by the processor, direct the processor to:
   identifying a third vector in the deformation vector field, wherein the third vector maps third data in the first interfractional patient state data to third data in the target region in the second interfractional patient state data; and
   storing the third vector in the modified deformation vector field.

24. The tangible, non-transitory, computer-readable medium of claim 21 comprising further instructions that, when executed by the processor, direct the processor to:
   adapt a treatment plan based upon the modified deformation vector field.

* * * * *